United States Patent [19]

Gönner et al.

[11] Patent Number: 4,818,489
[45] Date of Patent: Apr. 4, 1989

[54] DEVICE FOR SAMPLING BREATH AIR AT THE WORKPLACE

[75] Inventors: Winfried Gönner, Überlingen; Bruno Kolb, Owingen, both of Fed. Rep. of Germany; Gottfried Machata, Vienna, Austria

[73] Assignee: Bodenseewerk Perkin-Elmer & Co., GmbH, Überlingen, Fed. Rep. of Germany

[21] Appl. No.: 935,611

[22] Filed: Dec. 2, 1986

Related U.S. Application Data

[63] Continuation of Ser. No. 619,889, Jun. 12, 1984, abandoned.

[30] Foreign Application Priority Data

Jul. 1, 1983 [DE] Fed. Rep. of Germany ....... 3323720

[51] Int. Cl.$^4$ .................... G01N 33/14; G01N 33/48
[52] U.S. Cl. ....................... 422/84; 422/81; 422/100; 436/132; 436/900; 73/864; 73/864.51; 73/864.82; 128/719; 128/730; 141/17; 141/281; 141/283; 141/329
[58] Field of Search ............... 73/864, 864.18, 864.51, 73/864.82; 128/719, 730; 141/4, 17, 66, 281, 283, 329; 422/81, 83–85, 100; 436/132, 174, 180, 900

[56] References Cited

U.S. PATENT DOCUMENTS

| 3,661,528 | 5/1972 | Falk | 422/84 X |
| 3,764,270 | 10/1973 | Collier et al. | 422/84 |
| 3,765,402 | 10/1973 | Grabhorn | 141/329 X |
| 3,822,117 | 7/1974 | Bergh et al. | 422/84 X |
| 3,853,477 | 12/1974 | Block et al. | 422/85 |
| 4,041,994 | 8/1977 | Horwitz et al. | 141/329 X |
| 4,297,871 | 11/1981 | Wright et al. | 128/719 X |
| 4,346,584 | 8/1982 | Boehringer | 128/719 X |

FOREIGN PATENT DOCUMENTS

| 443829 | 5/1927 | Fed. Rep. of Germany | 141/66 |
| 2302134 | 10/1976 | France | 141/329 |
| 56-6137 | 1/1981 | Japan | 422/81 |

*Primary Examiner*—Barry S. Richman
*Assistant Examiner*—Timothy M. McMahon
*Attorney, Agent, or Firm*—Ronald G. Cummings; Francis L. Masselle; Edwin T. Grimes

[57] ABSTRACT

A pocket instrument for sampling breath air in situ, includes a microprocessor-controlled directional control valve with needles at an outlet to which needle the sample vessels are attached. The directional control valve is arranged to be connected through another outlet to the atmosphere and to a collecting chamber respectively, which collecting chamber is provided with a feeding device for accommodating and delivering the breath air.

11 Claims, 2 Drawing Sheets

DEVICE FOR SAMPLING BREATH AIR AT THE WORKPLACE

This is a continuation of co-pending application Ser. No. 619,889 filed on June 12, 1984 now abandoned.

BACKGROUND OF THE INVENTION

The present invention generally relates to a device and method for the in situ sampling of breath air at a predetermined minimum flow of breath air and, in particular, relates to such a device including a heatable housing having a mouthpiece, a directional control valve the inlet of which is connected to the mouthpiece, at least one needle connected to a first outlet of the directional control valve and an air-tightly closed sample vessel adapted to be pushed on the needle.

In general, methods for examining the breath air for alcohol are known, for example, (Dräger issue 322, 1982; Dräger-company brochure Alkcotest 7010, 1981). Therein, a minimum flow of breath air is conducted through a measuring instrument during a predetermined time interval. The measuring instrument includes a semiconductor sensor responding to alcohol or measures the alcohol absorption in the range of 3–4 μm. Therein, the condensation of humidity from the breath air is prevented by heating devices.

In another publication of N. Bilzer, M. Krämer, O. Grüner "A Method for the Determining of Poreath Alcohol with Multifract (Gaschromatography)" in "Proceedings Int. Conference for Alcohol, Drugs and Traffic Safety" 1980 vol. 2 page 691, publisher Almquist+Wikselt Int., Stockholm; a device for sampling breath air is described. The device is mounted in a heatable housing provided with a mouthpiece. The mouthpiece is connectable to the atmosphere and to a collecting chamber, respectively, via a two-way directional control valve. In the collecting chamber a piston is movable under the pressure of the breath air into a predetermined end position for accommodating a measured sample volume. The outlet of the collecting chamber is connected through a needle to an air-tightly closed sample vessel adapted to be attached to this needle, and through another two-way directional control valve closed during the sampling to a nitrogen source for the purpose of rinsing. The sample vessel is closed by a self-sealing membrane adapted to be pierced and is evacuated to accommodate the sample.

In another method the breath air is conducted directly through a measuring instrument which is matched for the particular application and the measurement is made in the air flow. It is, however, inappropriate to operate with a measuring instrument responding specifically to one component when the composition of the breath air at a working place has to be examined and qualitatively and quantitatively analysed for different components, which result, for example, from the metabolism of inhaled vapors. Therefore, it is more appropriate to take a sample of the breath air at the working place and to examine the breath air at another place.

The device described in the publication mentioned in the beginning is a laboratory instrument, which requires an evacuated sample vessel to be used. This device cannot be used at the work place itself.

SUMMARY OF THE INVENTION

Accordingly, it is one object of the present invention to provide a method and a device which can be used at a work place, in situ, and which is particularly adapted so that the activity of the person in question is minimally impeded even with frequent sampling.

The method for sampling breath air at a work place includes diverting a minimum flow of the breath air from the inlet of a directional control valve to the atmosphere i.e. a first position of the directional control valve, during a predetermined first time interval and, thereafter switching the directional control valve into a second position wherein the minimum flow of the breath air is conducted into a sample vessel which is air-tightly connected to the directional control valve. Hence, according to the method the device is first rinsed with the breath air before this air is conducted into the sample vessel.

In an advantageous embodiment of the method a minimum flow of the breath air is fed into a collecting chamber when the directional control valve is in an intermediated position after the predetermined first time interval has elapsed. After the collecting chamber has been filled and the directional control valve has been switched into the second position at least a part of the breath air contained in the collecting chamber is fed into the sample vessel. By this method it is possible to fill the sample vessel independently of the sampling proper and, if desired, to fill several sample vessels with the breath air for different examination procedures.

The sample vessel can be connected to the directional control valve prior to the sampling or alternatively, attached to the needle during the first time interval.

The device includes a sample vessel carrier for accommodating the sample vessel and is provided with a drive unit which is slidable within the housing relative to the needle. A second outlet of the directional control valve is adapted to be connected to the atmosphere through a pressure sensor, which sensor is adjustable to a predetermined minimum pressure, in a first position of the directional control valve, and a control controlled by the pressure sensor is provided, and arranged to move the sample vessel carrier relative to the directional control valve. The sample vessel is attachable to the needle and, after the first time interval has elapsed, the directional control valve is adapted to be switched into a second position to connect the mouthpiece to the first outlet. A limit switch can be provided for limiting the displacement of the sample vessel carrier which can be guided on guide bars and include a sample vessel support adjustable to the dimensions of the respective sample vessel.

In order to rinse the sample vessel it is advantageous if the directional control valve is provided with two needles at the first outlet and one needle is communicating with the atmosphere and if the sample vessel, after the first time interval has elapsed, is connected to the needles during a second time interval.

One device according to the invention includes a collecting chamber, for accommodating a breath air volume, connected to the directional control valve on the outlet side, the second outlet of the directional control valve is, in this embodiment, preferably connected to the atmosphere with valves controlled by the control. These valves are adapted to be closed after the first time interval has elapsed, and the collecting chamber is provided with a feeding device which is switched on by the control after the first time interval has elapsed. In such an embodiment the feeding device can be a piston pump and be in driving connection with a drive unit controllable by the control after the first interval has elapsed. A limit switch can be provided for limiting the piston displacement. The directional control valve can be adapted to be switched into an intermediate position for filling the collecting chamber after the first time interval has elapsed and, after the collecting chamber has been filled, can be switched into a second position, in which second position the collecting chamber is connected to the sample vessel.

Advantageously, the directional control valve is a 3/2-directional control valve i.e. having three inlets and two outlets. The sample vessel on the sample vessel carrier is aligned with the first outlet of the directional control valve, the collecting chamber is connected to the second outlet of the directional control valve via an intermediate piece which includes the pressure sensor and at least one bore controlled by a controlled valve for the communication with the atmosphere. In a preferred assembly, the above-mentioned elements form a linear arrangement in a housing, from which the mouthpiece extends laterally.

Thus, a device is provided which forms a compact and space-saving arrangement and which can be formed as a pocket instrument. As a consequence, by a mostly automatic control, a user's activity can be limited to the switching on and the insufflation of the breath air. The running-off of the program ensures that one or more unevacuated sample vessels can be filled with breath air, while avoiding any dilutions and pollutions.

Other objects and advantages will become apparent to those skilled in the art from the following detailed description read in conjunction with the appended claims and the drawings attached hereto.

BRIEF DESCRIPTION OF THE DRAWINGS

Embodiments of the invention are described in greater detail hereinafter with reference to the drawings, not drawn to scale, which includes.

DETAILED DESCRIPTION OF THE INVENTION

Figure 1:
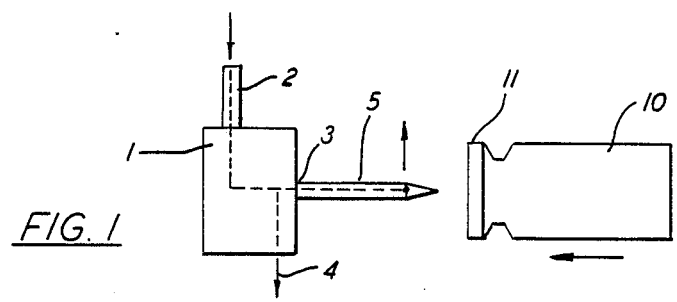
FIG. 1 which is a schematic illustration of a device embodying the principles of the present invention for implementing a first method.

A first embodiment of a device for the in situ sampling of breath air is schematically illustrated in FIG. 1. The device includes a directional control valve 1 having a mouthpiece 2 and two outlets, 3 and 4. The first outlet 3 is provided with a needle 5, for example, of the type of an injection needle, which is in gaseous communication with a sample vessel 10. The second outlet 4 is connected to the atmosphere. An evacuated sample vessel 10 is air-tightly closed by a self-sealing closure 11. Preferably, the closure 11 is formed from an aluminum-laminated rubber seal that can be attached to the needle 5 without loss of sealing.

In operation, the breath air flow is diverted from the mouthpiece 2 through the second outlet 4 to the atmosphere during a first time interval, for example, about 6 seconds. A pressure sensor, not shown FIG. 1, ensures that the directional control valve 1 flow is completed by a predetermined minimum flow of breath air. Thereby the directional control valve 1 is rinsed and at the same time it is ensured that deep air of the lungs (alveolar air) enters the sample vessel 10. That is, air which is in equilibrium with the blood in the air-cells of the lungs and the composition of which is unaffected by exchange reactions with the mucous membranes of the oral cavity. After the first time interval the directional control valve 1 is switched into a second position, either automatically or manually, in which second position the mouthpiece 2 communicates with the first outlet 3 such that the sample vessel 10 is filled with the breath air. Subsequently, the sample vessel 10 is removed from the needle 5.

Figure 2:
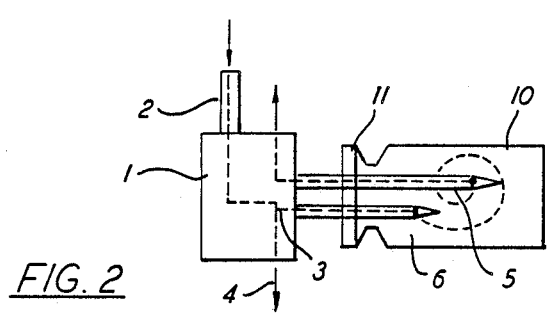
FIG. 2 which is a schematic illustration of a device embodying the principles of the present invention for implementing a second method.

In the schematic illustration of FIG. 2 a second embodiment is shown, which second embodiment is more appropriate for filling non-evacuated sample vessels 10. Two needles, 5 and 6, are attached to the first outlet 3 of the directional control valve 1. In this embodiment, the needles 5 and 6, are appropriate for introducing breath air into non-evacuated sample vessels 10. In this embodiment, the needle 6 is connected to the atmosphere outside the sample vessel 10 through another outlet of the directional control valve 1. After the first time interval has elapsed, the directional control valve 1 is switched into the second position and breath air is conducted through the sample vessel 10 during a second time interval. In this manner, the breath air displaces the air out of the sample vessel 10 which, rinsed by the breath air and filled with it, is removed from the needles, 5 and 6, after the second time interval has elapsed.

Figure 3:
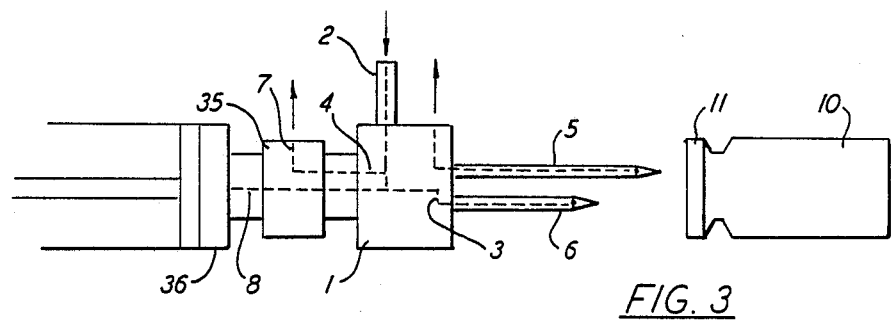
FIG. 3 which is a schematic illustration of a device embodying the principles of the present invention for implementing a third method.

A third embodiment of the method is illustrated in FIG. 3, in which a collecting chamber 36 having a feeding device in the form of a piston pump is provided. The collecting chamber 36 is adapted to accomodate a quantity of breath air sufficient for a sample vessel 10 or also a larger one. As before, the first outlet 3 of the directional control valve 1 is provided with two needles, 5 and 6, to which a sample vessel 10 is attached. In this embodiment, the directional control valve 1 includes one to three intermediate valves 35 which are connected to its second outlet 4. The intermediate valves 35 can be opened to the atmosphere and are connectable to the collecting chamber 36.

In operation, the directional control valve 1 is adjusted during the first time interval such that the breath air flow is diverted from the mouthpiece 2 of the directional control valve 1 and its second outlet 4 through the intermediate valves, or the intermediate valve 35, and its first outlet 7 to the atmosphere. After the first time interval has elapsed, the intermediate valve 35 is switched and the second outlet 8 is connected to the collecting chamber 36; the breath air flow is thusly fed into the collecting chamber 36 by the piston pump. After the collecting chamber 36 has been filled, the directional control valve 1 is switched from the intermediate position into a position in which the first outlet 3 is connected to the collecting chamber 36. Then, during a second time interval, the breath air is fed to the sample vessel 10 by activating the piston pump. With such a realization of the method several sample vessels 10 can be filled with the breath air to be examined by exchange at the needles, 5 and 6.

Figure 4:
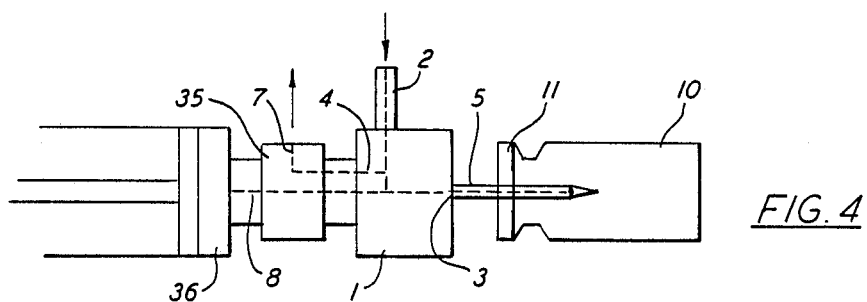
FIG. 4 which is a schematic illustration of a device for implementing a modified embodiment of the method diagramed in FIG. 3.

A variant of the method lastly described, which is schematically illustrated in FIG. 4, differs from the method illustrated in FIG. 3 in that only one needle 5 is arranged at the first outlet 3 of the directional control valve 1. The sample vessel 10 can be evacuated but also be filled with the breath air to a certain excess pressure by the piston pump.

Figure 5:
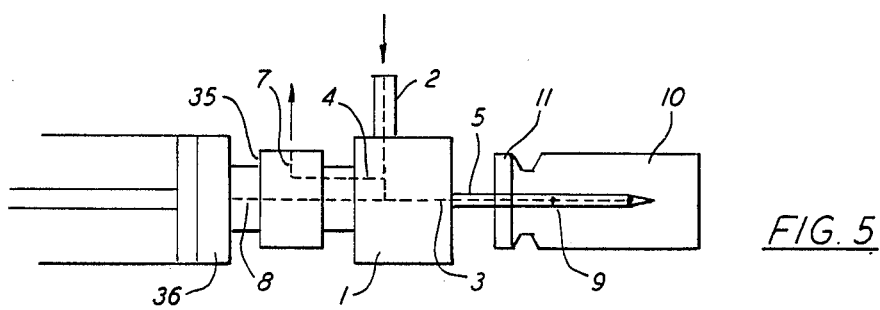
FIG. 5 which is a schematic illustration of a device for implementing a further modified embodiment of the method diagramed in FIG. 3.

In another varient of the method which is schematically illustrated in FIG. 5, the needle 5 is provided with a second outlet opening 9 enabling a pressure equalization in the sample vessel 10 to the atmosphere when the sample vessel 10 is removed from the needle 5.

Figure 6:
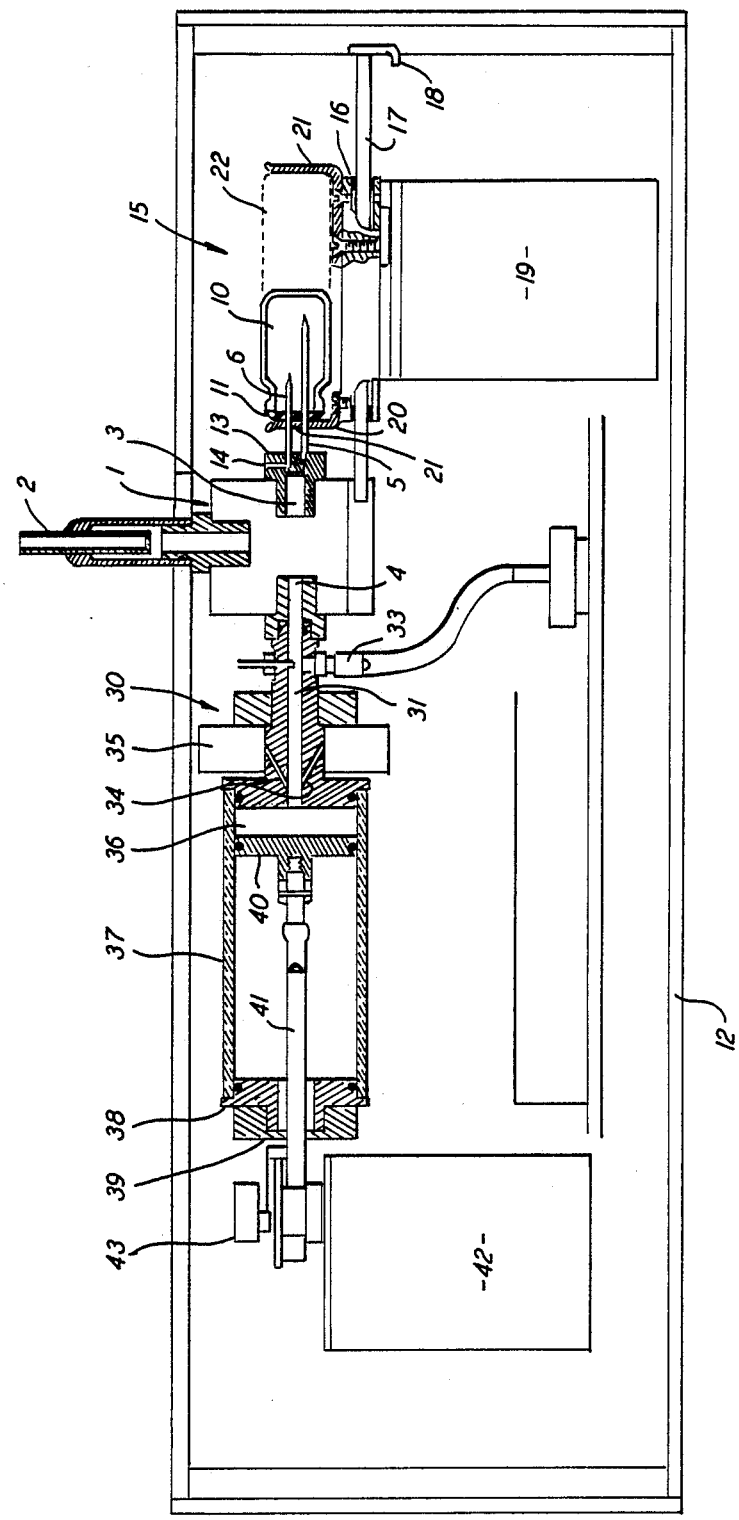
FIG. 6 which is a partial sectional illustration of a device embodying the principles of the invention for implementing the method diagramed in FIG. 3.

A device for carrying out the method illustrated by FIG. 3 is partially sectionally illustrated in detail in FIG. 6. This device is arranged in a housing 12 which is internally covered with heating mats, not shown in the drawing, by which heating mats the housing 12 is heated to temperatures in the range of 30° to 40° C. to avoid condensation. A 3/2-directional control valve, forming the directional control valve 1, is arranged in the housing 12. The valve 1 has an inlet, to which the mouthpiece 2, having a condensate collector, is connected, which mouthpiece 2 extends out of the housing 12. A first outlet 3 is provided for connection to the sample vessel 10 and a second outlet 4 is provided to which the collecting chamber 36 is connected via the intermediate valve 35.

In the area of the first outlet 3 a needle carrier 13 for the two needles, 5 and 6, is placed into engagement with the directional control valve 1; the longer needle 5 communicating with the mouthpiece 2, while the shorter needle 6 communicating with the inner chamber of the housing and thereby with the atmosphere via a transverse bore 14 in the needle carrier 13. A sample vessel carrier 15 with a ground plate 16 is associated with the first outlet 3. The ground plate 16 is guided on two guide bars 17 and which at one end are attached to the body of the directional control valve 1 and at the other end are attached to a support 18 fixed to the housing 12. A drive unit 19 is attached to the underside of the ground plate 16. Preferably, a rack is attached to the ground plate 16 between the housing-fixed guide bar 17, which rack engages a pinion driven by a stepping motor of the drive unit 19. A limit switch, not shown in FIG. 6, limits the displacement of the ground plate 16 on the guide bars 17 relative to the directional control valve 1, which limit switch can be formed, for example, by a microswitch or by light barriers.

An adjustable sample vessel carrier is located on the upper side of the ground plate 16, which carrier includes a front wall 20 facing the first outlet 3. The front wall 20 has an aperture 21 for passage therethrough of the needles, 5 and 6, and a back wall 21 remote from the first outlet 3, which back wall 21 is adjustable in the longitudinal direction of the ground plate 16 for adaptation to differently sized sample vessels 10. In FIG. 6 the sample vessel carrier 15 with a sample vessesl 10 having a capacity of 10 ml, for example, is shown in a position, in which the sample vessel 10 with the air-tight closure 11 is attached to the needles, 5 and 6, the back wall 21 is illustrated in a position for accommodating a sample vessel 10 with a capacity of 20 ml.

The intermediate piece 30 is sealingly connected at its first end to the second outlet 4 of the directional control valve 1, and, at its second end, to the collecting chamber 36 by sealing washers. A passage conduit 31, which connects the second outlet 4 to the collecting chamber 36, passes through the intermediate piece 30. In the area of the first end a pressure sensor 33 is inserted through the wall of the intermediate piece 30 into the passage conduit 31 which is provided with a tube port in the area of the pressure sensor 33, which tube port leads to a pressure switch located on a printed circuit board. In the area of the second end several lateral bores 34 (for example three, only two of which are shown in FIG. 6) extend from the passage conduit 31 to controlled valves 35 associated therewith, which bores connect the passage conduit 31 to the interior of the housing 12 and thereby to the atmosphere. In the illustrated embodiment the bores 34 extend backwardly at an angle to the flow direction.

The collecting chamber 36 is limited laterally by a sleeve 37 which is sealingly closed by sealing rings, at the first end thereof, by the second end of the intermediate piece 30, and at the second end thereof, by a closure 38 having a passage 39. A piston 40 sealingly engaging the inner wall of the sleeve 36 by a sealing ring is slidingly movable in the sleeve 36, which piston 40 is in drive connection with a driving unit 42 through a piston bar 41 which extends through the passage 39 of the closure 38. To this end a portion of the piston bar 41 is preferably formed as a rack which is in engagement with a pinion of the drive unit 42, which pinion is driven by a stepping motor. The drive unit 42 is affixed to the housing 12. A limit switch 43, formed, for example, by a microswitch or a light barrier, limits the displacement of the piston 40.

Futhermore, the device includes a microprocessor control for the sequences of operation, which includes conventional components and is programmed in a conventional way and therefore is not described in further detail herein. In the initial position of the device the first outlet 3, which leads to the sample vessel 10, is closed and the breath air insufflated through the mouthpiece 2 flows through the second outlet 4 and the passage conduit 31 of the intermediate piece 30, from which passage conduit 31 the breath air is diverted to the atmosphere through lateral bores 34. When a predetermined pressure has been reached at the pressure sensor 33, the controlled valves 35 are closed after a predetermined time interval, for example about 6 seconds; at the same time the drive unit 42 is energized and the piston 40 displaced in the direction towards the closure 38. When the limit switch 43 responds, the stepping motor of the drive unit 42 is stopped and the directional control valve 1 is switched over into a position in which the collecting chamber 36, now filled with breath air, is connected to the sample vessel 10. Then the stepping motor of the drive unit 42 is reversed, whereby the breath air accommodated in the collecting chamber 36 is fed through the sample vessel 10 into the interior of the housing 12 and thereby to the atmosphere. Subsequently, the stepping motor of the drive 19 unit is operated and the sampled vessel carrier 15 with the sample vessel 10, now rinsed and filled with the breath air, is removed from the needles, 5 and 6. The device is ready for a new sampling after the piston 40 has reached its initial position, in which the piston 40 engages the intermediated piece 30 completely at the right, a new sample vessel 10 is inserted into the sample vessel carrier 15 and the new sample vessel 10 is pushed on the needles, 5 and 6, by the driving unit 19.

With appropriate dimensions of the sample vessels 10 and of the collecting chamber 36, multiple sampling from the collecting chamber 36 is quite feasible. In such an instance, the piston 40 can be further advanced with a reduced speed or can be stopped for the period during the changing of the sample vessel 10.

Altogether a compact arrangement of all components of the device is obtained, which compactness permits the entire device to be constructed as a pocket instrument, which can be arranged for connection to the main or to an independent power source.

The present invention has been described herein by use of a number of exemplary embodiments which are not deemed limiting. Consequently, the present invention is deemed limited only be the appended claims and the reasonable interpretation thereof.

What is claimed is:

1. An automatic breath air sampling device comprising
   a directional control valve having an inlet, a first outlet and a second outlet,
   a mouthpiece communicating with said inlet for exhaling breath air into said control valve,
   needle means communicating with said first outlet for conducting breath air into a sealed sample vessel,
   a sealed sample vessel for holding a breath air sample for testing, said vessel being adapted to be pushed onto said needle means to receive breath air therefrom,
   a sample vessel carrier means for movably mounting said vessel and for driving said vessel into fluid communication with said needle means thereby enabling said vessel to receive a breath air sample,
   said control valve being switchable between at least first and second operating positions with said control valve being configured in said first position for diverting breath air from said inlet to discharge from said second outlet so as to rinse said control valve of dilutants and pollutants with breath air prior to sampling for purpose of preventing introduction of dilutants and pollutants into the sample vessel in said second position and said control valve being configured in said second position for discharging sample breath air through said needle means into said sample vessel,
   pressure sensor means for sensing a predetermined minimum flow of breath air from said second outlet when said control valve is switched to said first position,
   timing means for establishing a fixed predetermined time interval after said pressure sensor means senses said predetermined minimum flow, said time interval being predetermined for adequate rinsing of said control valve of sample dilutants and pollutants with breath air, and
   control means for controlling said vessel carrier means to drive said vessel into communication with said needle means and for switching said control valve to said second position after said timing means determines said time interval has elasped where said control valve is rinsed of dilutants and pollutants.

2. The device of claim 1 wherein said control valve is configured to divert breath air from said inlet to said second outlet in said first position and from said inlet to said first outlet in said second position.

3. The device of claim 1 wherein said control means controls said vessel carrier means to drive said vessel into communication with said needle means upon said pressor sensor means sensing a predetermined minimum flow rate.

4. The device of claim 1 further comprising means for exhausting said second outlet of said control valve to atmosphere during said first time interval.

5. The device of claim 4 wherein
   said needle means comprises two needles,
   and said device further comprises means for determining second predetermined time interval sufficient to rinse said a sample vessel of dilutants and pollutants with breath air from said mouthpiece,
   said control valve being configured for a third intermediate operating position with (a) breath air being diverted from said inlet to said second outlet in said first position, (b) breath air being diverted from said inlet through said needle means into said vessel in said second position, and (c) one of said needles being exhausted to atmosphere and breath air being diverted for said inlet through said other needle into said vessel in said third position, and
   said control means having means for switching said control valve to said third position at the end of said first time interval and actuating said means for determining a second time interval and for switching said control valve to said second position at the end of said second time interval.

6. The device of claim 1 further comprising
   a collecting chamber for holding breath air,
   connector means for providing fluid communication between said second outlet of said control valve and said collecting chamber, said connector means having a intermediate valve and a bore providing communication between said second outlet and atmosphere through said intermediate valve,
   feeding means connected to said chamber for feeding breath air into and from said collecting chamber, and
   said control means further comprising means for controlling said intermediate valve to be open during said time interval so as to discharge breath air from said second outlet of said control valve to atmosphere and to be closed at the end of said time interval and means for controlling said feeding means for feeding breath air into said collecting chamber when said intermediate valve is closed at the end of said time interval and for feeding breath air from said collecting chamber when said control valve is switched to said second position so as to feed breath air from said collecting chamber into said sample vessel.

7. The device of claim 6 wherein
   said collecting chamber is of sufficient capacity for holding breath air for filling a plurality of sample vessels and
   said control means further comprises means for controlling said control valve, said feeding means and said vessel carrier means for filling a plurality of sample vessels in seriatim from said collecting chamber.

8. The device of claim 6 comprising an approximately pocket-size sampling device housing means providing a self-contained portable housing for said breath air sampling device with said control means comprising microprocessor means for automatic control.

9. The device of claim 6 wherein
   said needle means comprises two needles,
   and said device further comprises means for determining a second predetermined time interval when said feeding means begins feeding breath air into said sample vessel, said second time interval being sufficient to rinse said sample vessel of dilutants and pollutants with breath air from said collecting chamber, and exhaust means for connecting one of said needles to atmosphere for said second time period for rinsing said sample vessel with breath air prior to filling the sample vessel with breath air to be tested and wherein said control means further comprises means for disengaging said vessel from said needle means after said second interval has elasped.

10. The device of claim 6 wherein said feeding means comprises a piston pump configured for reciprocal movement within said collecting chamber.

11. The device of claim 6 wherein said control valve is configured to divert breath air from said inlet to said second outlet in said first position and from said second outlet to said first outlet in said second position.

* * * * *